US012508383B2

(12) United States Patent
Zhou et al.

(10) Patent No.: US 12,508,383 B2
(45) Date of Patent: Dec. 30, 2025

(54) RESPIRATORY MASK AND VENTILATION THERAPY DEVICE

(71) Applicant: CAREMEDI TECHNOLOGY CO., LTD., Tianjin (CN)

(72) Inventors: Mingzhao Zhou, Beijing (CN); Yajie Wang, Beijing (CN); Zhi Zhuang, Beijing (CN)

(73) Assignee: CAREMEDI TECHNOLOGY CO., LTD., Tianjin (CN)

( * ) Notice: Subject to any disclaimer, the term of this patent is extended or adjusted under 35 U.S.C. 154(b) by 1023 days.

(21) Appl. No.: 17/419,498

(22) PCT Filed: Dec. 27, 2019

(86) PCT No.: PCT/CN2019/129341
§ 371 (c)(1),
(2) Date: Jun. 29, 2021

(87) PCT Pub. No.: WO2020/135760
PCT Pub. Date: Jul. 2, 2020

(65) Prior Publication Data

US 2022/0088336 A1 Mar. 24, 2022

(30) Foreign Application Priority Data

Dec. 29, 2018 (CN) ........................ 201811646330.2

(51) Int. Cl.
*A61M 16/06* (2006.01)
*A61M 16/08* (2006.01)

(52) U.S. Cl.
CPC .... *A61M 16/0622* (2014.02); *A61M 16/0672* (2014.02); *A61M 16/0816* (2013.01); *A61M 2205/42* (2013.01)

(58) Field of Classification Search
CPC .......... A61M 16/0622; A61M 16/0672; A61M 16/06; A61M 16/08–0891;
(Continued)

(56) References Cited

U.S. PATENT DOCUMENTS 6,412,487 B1 7/2002 Gunaratnam et al.
8,967,146 B2* 3/2015 Veliss ............... A61M 16/0622 128/206.28
(Continued)

FOREIGN PATENT DOCUMENTS

AU 2015234317 10/2015
CN 101987221 A 3/2011
(Continued)

OTHER PUBLICATIONS

WIPO, International Search Report for PCT/CN2019/129341, Mar. 26, 2020.
(Continued)

*Primary Examiner* — Timothy A Stanis
*Assistant Examiner* — Kira B Daher
(74) *Attorney, Agent, or Firm* — Hodgson Russ LLP

(57) ABSTRACT

The present disclosure relates to the field of ventilation therapy apparatus, and discloses a respiratory mask and a ventilation therapy apparatus. The respiratory mask includes a cushion assembly, an elbow assembly, and a connecting assembly arranged between the cushion assembly and the elbow assembly. The cushion assembly includes a cup, the connecting assembly includes a frame and a connector, the elbow assembly includes an elbow, an exhaust passage is formed between the connector and the frame and/or between the cup and the frame, and the exhaust passage is arranged to be able to guide a respiratory exhaust gas to be diverged and discharged all around the elbow.

11 Claims, 12 Drawing Sheets

(58) Field of Classification Search
CPC ............ A61M 16/024; A61M 16/0605; A61M 16/0683; A61M 16/00; A61M 16/0003; A61M 2205/42; A61M 39/10; A61M 2039/1027
See application file for complete search history.

(56) References Cited

U.S. PATENT DOCUMENTS

| | | | | |
|---|---|---|---|---|
| 10,675,430 | B2 * | 6/2020 | Goldspink ........ | A61M 16/0683 |
| 2004/0112385 | A1 * | 6/2004 | Drew .................... | A61M 39/10 128/207.12 |
| 2005/0199240 | A1 * | 9/2005 | Hall .................. | A61M 16/0825 128/206.26 |
| 2007/0181130 | A1 * | 8/2007 | Worley ............. | A61M 16/0875 128/207.14 |
| 2008/0210241 | A1 * | 9/2008 | Schulz .................. | A61M 16/06 128/206.21 |
| 2009/0241961 | A1 * | 10/2009 | McAuley .......... | A61M 16/0816 128/207.18 |
| 2014/0150798 | A1 * | 6/2014 | Fong ................. | A61M 16/0825 128/206.21 |
| 2016/0008558 | A1 | 1/2016 | Huddart et al. | |
| 2018/0104431 | A1 * | 4/2018 | Ng .................... | A61M 16/0875 |
| 2018/0250486 | A1 * | 9/2018 | Amarasinghe .... | A61M 16/0816 |

FOREIGN PATENT DOCUMENTS

| | | | |
|---|---|---|---|
| CN | 102458547 | A | 5/2012 |
| CN | 103189092 | | 7/2013 |
| CN | 103354752 | | 10/2013 |
| CN | 103764213 | A | 4/2014 |
| CN | 105079933 | | 11/2015 |
| CN | 204890882 | U | 12/2015 |
| CN | 105413035 | | 3/2016 |
| CN | 108348722 | A | 7/2018 |
| CN | 108348723 | | 7/2018 |
| CN | 109568756 | | 4/2019 |
| CN | 209864957 | | 12/2019 |
| EP | 2818195 | A1 | 12/2014 |
| EP | 3300761 | A1 | 4/2018 |
| JP | 2009050707 | | 3/2009 |
| JP | 2013163076 | | 8/2013 |
| JP | 2013540032 | | 10/2013 |
| JP | 2014517735 | | 7/2014 |
| JP | 2014520576 | | 8/2014 |
| JP | 2018167080 | | 11/2018 |
| WO | 2012123891 | | 9/2012 |
| WO | 2013006899 | | 1/2013 |

OTHER PUBLICATIONS

CNIPA, Second Office Action for CN Application No. 201811646330.2, Jun. 27, 2024.

EPO, Extended European Search Report for EP Application No. 19904717.6, Jan. 12, 2022.

JPO, Notice of Reasons for Refusal for JP Application No. 2021-538481, Jun. 28, 2022.

CNIPA, Office Action for CN Application No. 201811646330.2, Dec. 19, 2023.

* cited by examiner

RESPIRATORY MASK AND VENTILATION THERAPY DEVICE

CROSS-REFERENCE TO RELATED APPLICATIONS

The present application is a U.S. national phase entry under 35 U.S.C. § 371 of International Application PCT/CN2019/129341, filed on Dec. 27, 2019, which claims priority to Chinese Patent Application No. CN201811646330.2, filed on Dec. 29, 2018, the entire disclosures of which are incorporated herein by reference.

TECHNICAL FIELD

The present disclosure relates to the field of ventilation therapy apparatus; in particular, the present disclosure relates to a respiratory mask and a ventilation therapy apparatus with the respiratory mask.

BACKGROUND

Non-invasive positive pressure ventilation has been widely used in the treatment of diseases such as obstructive sleep apnea (OSA), chronic obstructive pulmonary emphysema (COPD), etc. It is no longer required to insert a hose into patient's airway through a surgical operation; instead, a blower is used to deliver a continuous positive airway pressure (CPAP) or a variable positive airway pressure to the patient's airway through a pipeline and a patient interface device.

The patient interface device in non-invasive ventilation treatment usually includes a respiratory mask such as a nasal mask, an oronasal mask, a nasal pillow mask, and a full-face mask. A typical structure of the respiratory mask includes a frame, a cushion, an elbow, a connector, a headband, and so on. The cushion is fixed to the frame so that a gas chamber is formed by the cushion together with the frame, the elbow is connected to the frame through the connector to deliver a therapeutic gas into the gas chamber, and the headband is connected to the patient's head to fix the respiratory mask at a proper position of the patient's head. In use, the cushion is in contact with the patient's face to achieve sealing against the face, and the patient's mouth and/or nose are located in the gas chamber.

Since respiratory exhaust gas needs to be discharged out of a respiratory mask during use thereof, the respiratory mask is usually provided with exhaust holes in order to discharge the respiratory exhaust gas smoothly. However, the exhaust holes in the existing respiratory masks are usually provided in an elbow or frame. In order to ensure a volume of exhaust gas, these exhaust holes usually have a large hole diameter; therefore, the respiratory mask has a louder exhaust noise and the discharged gas will affect the bed partner.

In order to solve the above problems, some existing respiratory masks are provided with small holes for discharging the gas, such as the respiratory masks shown in FIGS. 1 and 2, in which small exhaust holes 31' are centralizedly arranged in clusters in the elbow 3' (see FIG. 1) or in the frame 1' (see FIG. 2). However, because the diameter and molding of the small holes are greatly affected by molds, it is difficult to produce the holes and the cost is high; and due to spatial limitations, the direction in which the small holes discharge the gas will still blow the airflow to the bed partner, thus affecting sleeping quality of the patient himself/herself and the bed partner.

SUMMARY

An object of the present disclosure is to provide a respiratory mask and a ventilation therapy apparatus with the respiratory mask, so as to reduce the exhaust noise of the respiratory mask and meanwhile prevent the discharged airflow from being blown to the bed partner.

In order to achieve the above object, an aspect of the present disclosure provides a respiratory mask, the respiratory mask comprises a cushion assembly, an elbow assembly, and a connecting assembly arranged between the cushion assembly and the elbow assembly, the cushion assembly comprises a cup, the connecting assembly comprises a frame and a connector, and the elbow assembly comprises an elbow, and wherein an exhaust passage is formed between the connector and the frame and/or between the cup and the frame, and the exhaust passage is arranged to be able to guide a respiratory exhaust gas to be diverged and discharged all around the elbow. In the respiratory mask of the present disclosure, an exhaust passage is provided between a connector and a frame and/or between a cup and the frame, and the exhaust passage is arranged to guide respiratory exhaust gas to be diverged and discharged all around an elbow, so that no matter which direction a patient wearing the respiratory mask faces, the airflow would not be blown to his/her bed partner. In addition, since the airflow is diverged and discharged in an annular manner, the exhaust noise can be reduced effectively.

Optionally, the connector has an outer wall surface for connecting with the frame, and the exhaust passage is formed between the outer wall surface and the frame.

Optionally, the frame comprises an installation cavity for installing the connector, the installation cavity comprises a cylindrical cavity and a truncated cone cavity that are coaxial and in communication with each other, the truncated cone cavity is arranged close to the elbow, and the frame further comprises a first wall surface for defining the cylindrical cavity and a second wall surface for defining the truncated cone cavity; and the outer wall surface of the connector comprises a cylindrical surface corresponding to the first wall surface and a truncated cone surface corresponding to the second wall surface, gaps are provided in a radial direction of the installation cavity between the first wall surface and the cylindrical surface as well as between the second wall surface and the truncated cone surface, and the gaps form the exhaust passage. With the structural features of the second wall surface and the truncated cone surface, the rear exhaust section is formed into a horn shape surrounding the elbow, so that the respiratory exhaust gas is diverged and discharged all around the elbow.

Optionally, a diameter of the truncated cone cavity increases gradually in a direction away from the cylindrical cavity, and the first wall surface and the second wall surface are transitionally connected by a first arc; and/or the cylindrical surface and the truncated cone surface are transitionally connected by a second arc. Which may ensure flowing continuity and smoothness of the respiratory exhaust gas, reduce flow resistance and reduce noise.

Optionally, an included angle β between a generatrix of the truncated cone cavity and a bottom surface of the truncated cone cavity is 0°-75°, preferably 10°-30°. The included angle of this range may prevent the discharged airflow from disturbing the bed partner.

Optionally, a second protrusion is protrudingly formed on the truncated cone surface, and a second surface of the second protrusion facing away from the truncated cone surface is arranged to abut against the second wall surface; or a second protrusion is protrudingly formed on the second wall surface, and a second surface of the second protrusion facing away from the second wall surface is arranged to abut against the truncated cone surface. The second protrusion may improve the reliability of assembling the connector with the frame and reduce the degree of freedom of an axial movement of the connector after assembly.

Optionally, a generatrix of the truncated cone surface is parallel to a generatrix of the truncated cone cavity, and a protruding height of the second protrusion is 0.05 mm-0.6 mm, preferably 0.05 mm-0.2 mm; and/or the truncated cone surface or the second wall surface is provided with a plurality of the second protrusions spaced apart in a circumferential direction of the truncated cone surface or the second wall surface. Which may further ensure the volume of exhaust gas and reduce the exhaust noise, and the second protrusions may further enhance the above effect.

Optionally, the connector is connected to the frame through a snap-fit structure, and the snap-fit structure comprises a first buckle provided on the outer wall surface and a second buckle provided on the frame and fitting with the first buckle.

Optionally, the first buckle is an annular boss protrudingly formed on the cylindrical surface and extending in a circumferential direction of the cylindrical surface, the second buckle is a first protrusion protrudingly formed on the first wall surface and the connector bears against the first protrusion through the annular boss.

Optionally, a width of the first protrusion gradually increases in a direction toward the annular boss in an axial direction of the cylindrical cavity, to achieve a firm snap-fit with the annular boss, and increase the ability of bearing pressure of the first protrusion, which may facilitate discharge of the respiratory exhaust gas; and/or an end of a first surface of the first protrusion facing away from the first wall surface, which is close to the second wall surface, extends to the second wall surface and the end is coplanar with the second wall surface, to achieve a smooth transition of the airflow between the front exhaust section and the rear exhaust section.

Optionally, a plurality of the first protrusions is provided on the first wall surface, and the plurality of the first protrusions is spaced apart in a circumferential direction of the first wall surface; and/or the respiratory mask comprises an anti-rotation structure for preventing the connector from rotating relative to the frame, which may prevent the connector from rotating relative to the frame.

Optionally, the anti-rotation structure comprises a flange protrudingly formed on the cylindrical surface and a groove formed on the first protrusion for embedding by the flange.

A respiratory mask is provided according to the present disclosure, comprising a cushion assembly, an elbow assembly, and a connecting assembly arranged between the cushion assembly and the elbow assembly, wherein the connecting assembly comprises a frame and a connector, the elbow assembly comprises an elbow, an exhaust passage is formed between the connector and the frame and/or between the cushion assembly and the frame, and the exhaust passage is arranged to be able to guide a respiratory exhaust gas to be diverged and discharged all around the elbow. So that no matter which direction a patient wearing the respiratory mask faces, the airflow would not be blown to his/her bed partner. In addition, since the airflow is diverged and discharged in an annular manner, the exhaust noise can be reduced effectively.

In another aspect of the present disclosure, a ventilation therapy apparatus is provided, comprising a host for generating a therapeutic gas, and a respiratory mask in communication with a gas outlet of the host, wherein the respiratory mask is the above respiratory mask.

In the respiratory mask of the present disclosure, an exhaust passage is provided between a connector and a frame and/or between a cup and the frame, and the exhaust passage is arranged to guide respiratory exhaust gas to be diverged and discharged all around an elbow, so that no matter which direction a patient wearing the respiratory mask faces, the airflow would not be blown to his/her bed partner. In addition, since the airflow is diverged and discharged in an annular manner, the exhaust noise can be reduced effectively.

Other features and advantages of the present disclosure will be described in detail in the following specific embodiments.

BRIEF DESCRIPTION OF THE DRAWINGS

Accompanying drawings are provided to enable a further understanding of the present disclosure. They constitute a part of the specification, and are used to interpret the present disclosure together with the following specific embodiments. However, the drawings do not constitute a limitation to the present disclosure. In the drawings.

REFERENCE SIGNS

1: frame; 11: first wall surface; 111: first protrusion; 112: first surface; 113: groove; 114: side surface; 12: second wall surface; 13: first arc; 2: connector; 21: inner wall surface; 22: cylindrical surface; 221: annular boss; 222: flange; 23: truncated cone surface; 231: second protrusion; 24: second arc; 25: first convex portion; 26: second convex portion; 27: mark portion; 3: elbow; 4: exhaust passage; 41: front exhaust section; 42: rear exhaust section; 5: cushion; 6: cup; 61: interface portion; 1': frame; 3': elbow; 31': small exhaust hole.

DETAILED DESCRIPTION

Specific embodiments of the present disclosure will be described in detail below with reference to the accompanying drawings. It should be understood that the specific embodiments described herein are only used to illustrate and interpret the present disclosure, and are not used to limit the present disclosure.

Figure 1:
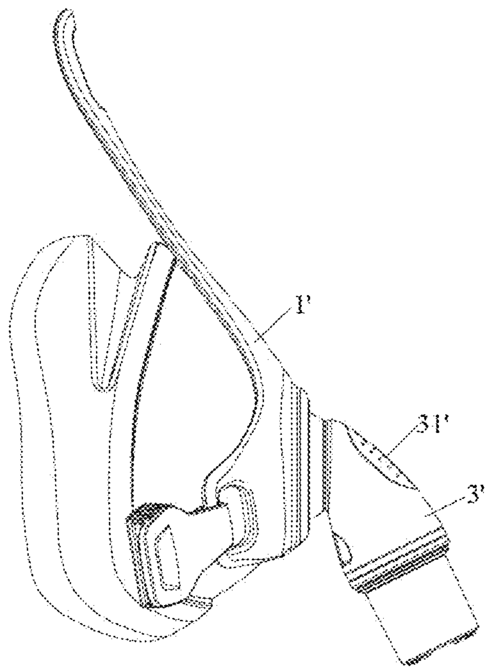
FIG. 1 is a schematic structural view of a respiratory mask in the prior art.
Figure 2:
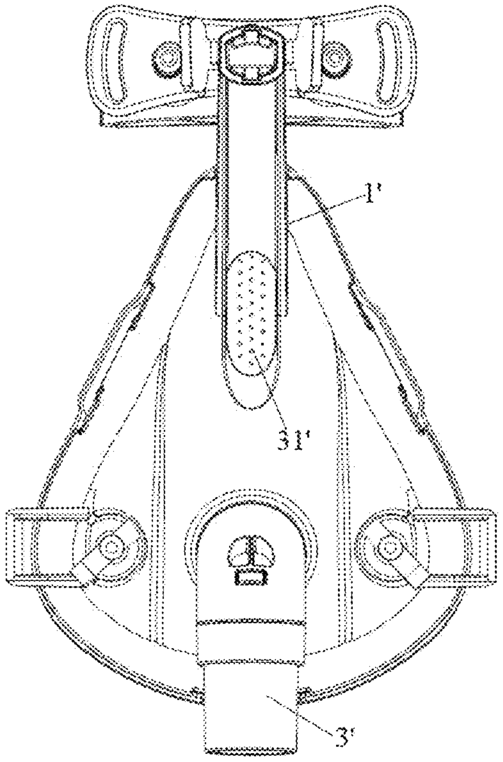
FIG. 2 is a schematic structural view of another respiratory mask in the prior art.

In the present disclosure, unless otherwise defined, terms for describing orientations such as "top" and "bottom" refer to the orientations shown in FIG. 1. Terms "inside" and "outside" refers to the inside and outside relative to the contour of each component itself.

An aspect of the present disclosure provides a respiratory mask, which includes a cushion assembly, an elbow assembly, and a connecting assembly arranged between the cushion assembly and the elbow assembly. The cushion assembly includes a cup 6, the connecting assembly includes a frame 1 and a connector 2, and the elbow assembly includes an elbow 3. An exhaust passage 4 is formed between the connector 2 and the frame 1 and/or between the cup 6 and the frame 1, and the exhaust passage 4 is arranged to be able to guide a respiratory exhaust gas to be diverged and discharged all around the elbow 3.

With the exhaust passage 4 provided between the connector 2 and the frame 1 and/or between the cup 6 and the frame 1 and arranged to guide the respiratory exhaust gas to be diverged and discharged all around the elbow 3, the respiratory mask of the present disclosure can prevent an airflow from being blown to the bed partner no matter which direction a patient wearing the respiratory mask is facing, and because the airflow is diverged and discharged in an annular manner, the exhaust noise can be effectively reduced.

Figure 3:
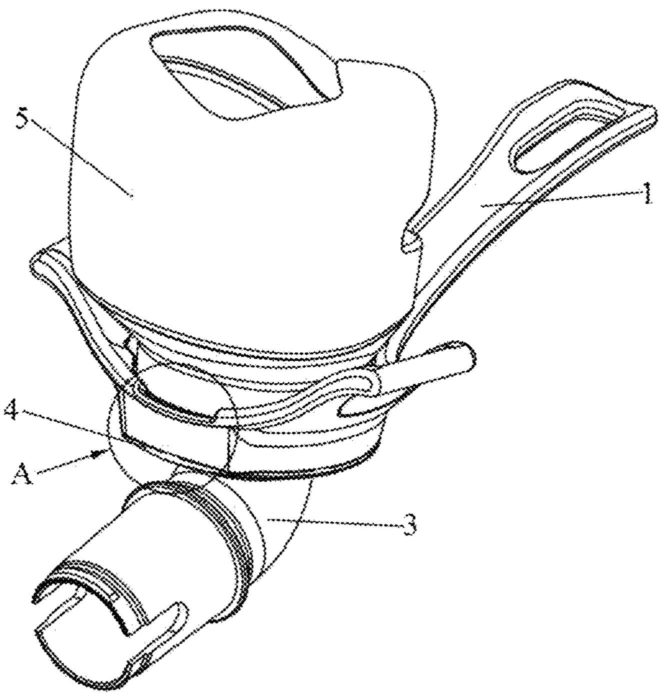
FIG. 3 is a perspective view of an embodiment of a respiratory mask of the present disclosure.
Figure 4:
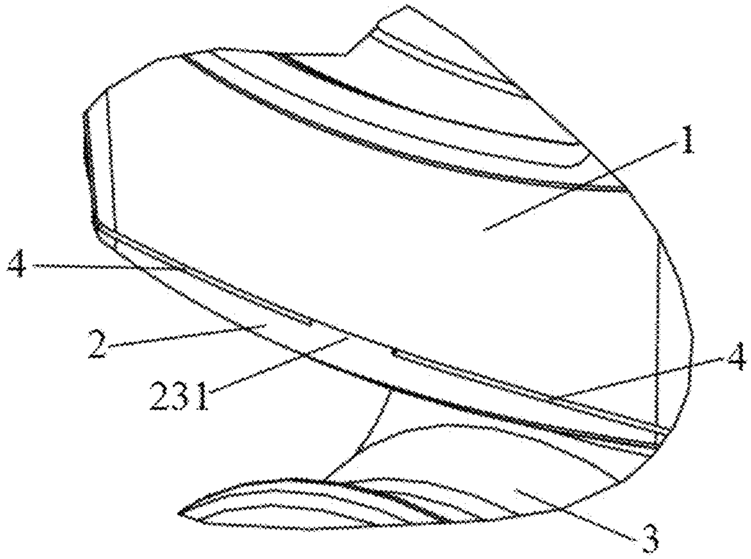
FIG. 4 is an enlarged view of part A in FIG. 3.
Figure 6:
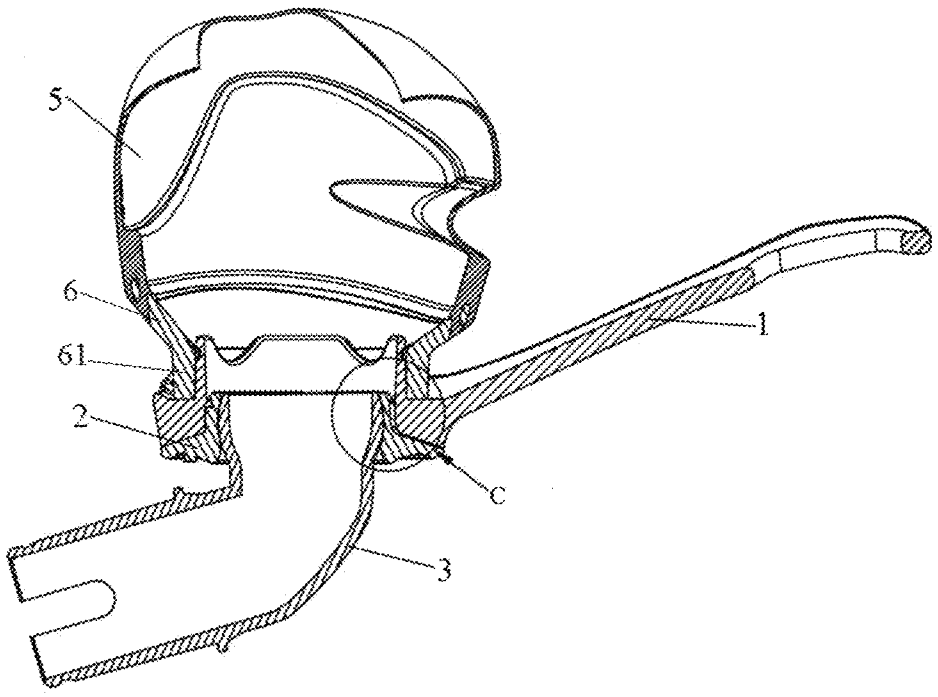
FIG. 6 is a cross-sectional view taken along line B-B in FIG. 5.

For example, as shown in FIGS. 3 and 6, it should be understood that regarding the aforementioned, the cushion assembly may further include a cushion 5 installed on a side of the cup 6 facing away from the frame 1. The cushion 5, the cup 6 and the frame 1 together form a gas chamber, and the elbow 3 is connected with the frame 1 through the connector 2 to deliver a gas into the gas chamber. When in use, the cushion 5 is in contact with a patient's face and achieves sealing against the face. The patient's mouth and/or nose are located in the gas chamber. Therefore, the exhaust passage 4 is in communication with the gas chamber, and the respiratory exhaust gas generated by the patient will first enter the gas chamber, and then is discharged through the exhaust passage 4. In addition, the respiratory exhaust gas is diverged and discharged all around the elbow 3, which may be understood in the following way: the respiratory exhaust gas is discharged in a circumferential direction of the elbow 3 and at a certain angle with an axial direction of the elbow 3. The circumferential direction and the axial direction of the elbow 3 are defined with respect to an end of the elbow 3 that is connected to the connector 2 (see FIGS. 3 and 4).

It should be noted that the connector 2 and the elbow 3 may each be a single piece, or the connector 2 and the elbow 3 may also be integral. The connector 2 may be made of polypropylene (PP) material or polycarbonate (PC) material. Preferably, the connector 2 is less rigid than the frame 1 and/or the elbow 3, so as to reduce abnormal sound caused by rotation between the elbow 3 and the frame 1 and increase smoothness of the rotation.

In addition, as shown in FIG. 6, it should be noted that the cup 6 may include an interface portion 61, and the cup 6 may be connected to a connecting assembly through the interface portion 61. If the exhaust passage 4 is provided between the cup 6 and the frame 1 in the respiratory mask of the present disclosure, the exhaust passage 4 may be arranged between the interface portion 61 and the frame 1. The interface portion 61 may be arranged to extend from the cup 6 toward a connection side of the connecting assembly (see FIG. 6), or extend from the cup 6 in a direction away from the connection side of the connecting assembly. Preferably, the interface portion 61 is arranged to extend from the cup 6 in the direction away from the connection side of the connecting assembly so as to improve connection stability between the interface portion 61 and the connecting assembly and to reduce a volume of the respiratory mask.

Figure 5:
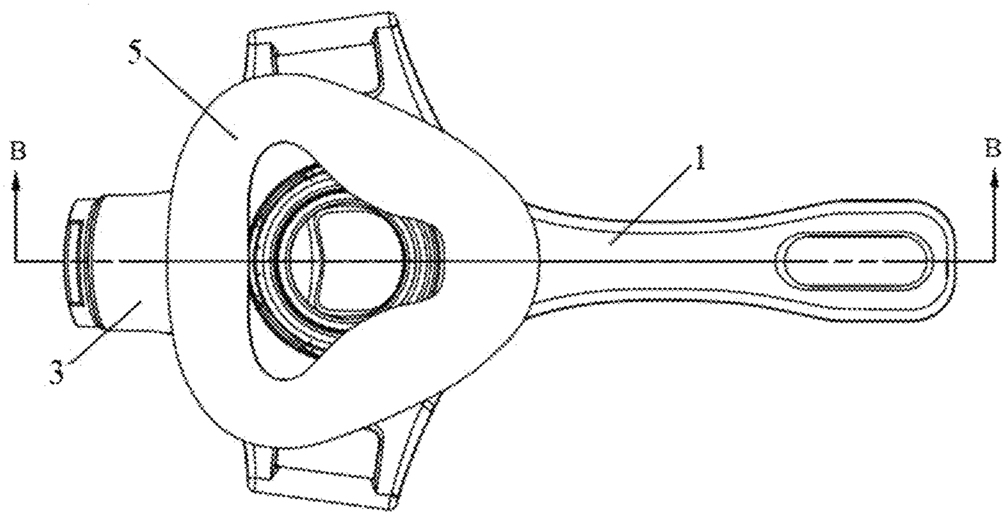
FIG. 5 is a top view of the respiratory mask in FIG. 3.

In the present disclosure, for the connection of the connector 2 with the elbow 3 and the frame 1, according to an embodiment as shown in FIGS. 5 and 6, the connector 2 may have an inner wall surface 21 for connecting with the elbow 3 and an outer wall surface for connecting with the frame 1. According to an embodiment of the present disclosure, the exhaust passage 4 may be formed between the outer wall surface and the frame 1.

Figure 9:
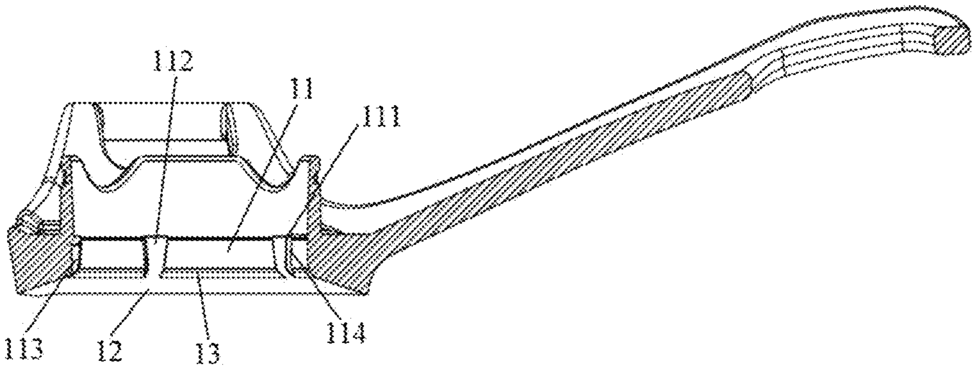
FIG. 9 is a cross-sectional view taken along line D-D in FIG. 8.
Figure 11:
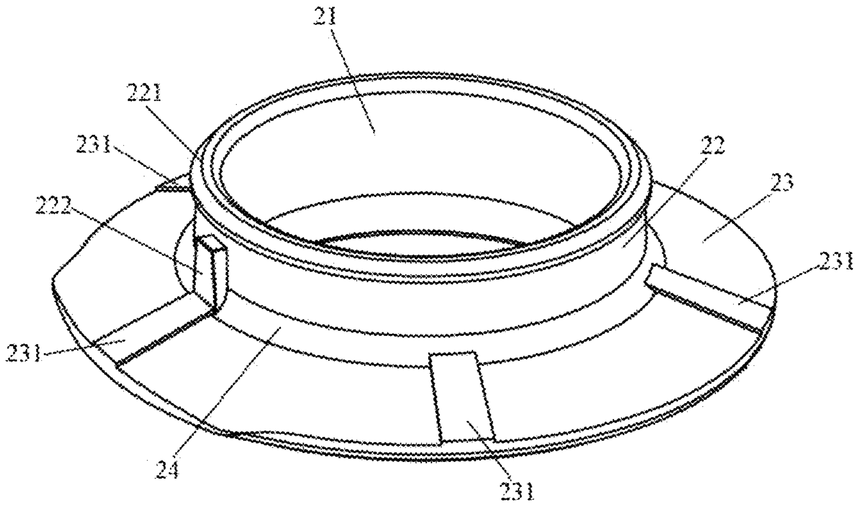
FIG. 11 is a perspective view of an embodiment of a connector of the present disclosure.
Figure 13:
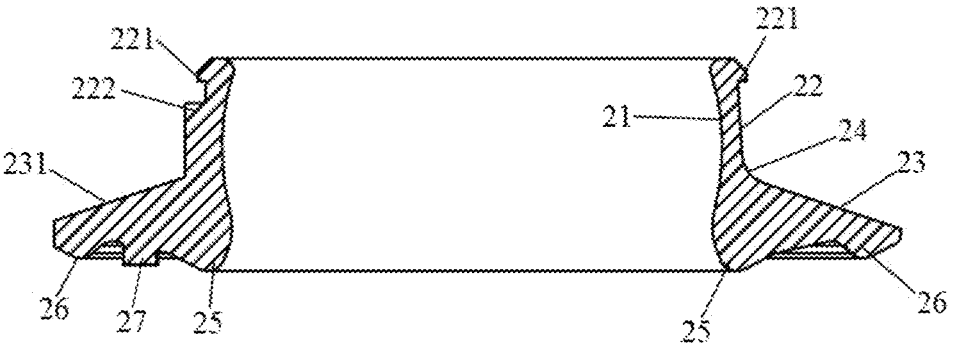
FIG. 13 is a cross-sectional view taken along line F-F in FIG. 12.

Further, according to an embodiment of the exhaust passage 4 of the present disclosure, as shown in FIG. 9, the frame 1 may include an installation cavity for installing the connector 2. The installation cavity includes a cylindrical cavity and a truncated cone cavity that are coaxial and in communication with each other. The truncated cone cavity is located close to the elbow 3 (i.e., a lower end shown in FIG. 9), and has a diameter increasing gradually in a direction away from the cylindrical cavity (i.e., from top to bottom as shown in FIG. 9). The frame 1 further includes a first wall surface 11 for defining the cylindrical cavity and a second wall surface 12 for defining the truncated cone cavity; as shown in FIGS. 6, 11 and 13, the outer wall surface of the connector 2 may include a cylindrical surface 22 corresponding to the first wall surface 11 and a truncated cone surface 23 corresponding to the second wall surface 12. Gaps are provided in a radial direction of the installation cavity between the first wall surface 11 and the cylindrical surface 22 as well as between the second wall surface 12 and the truncated cone surface 23. The gaps form the exhaust passage 4. It can be understood that the gap between the first wall surface 11 and the cylindrical surface 22 and the gap between the second wall surface 12 and the truncated cone surface 23 are in communication with each other. The exhaust passage 4 may include a front exhaust section 41 formed by the gap between the first wall surface 11 and the cylindrical surface 22, and a rear exhaust section 42 formed by the gap between the second wall surface 12 and the truncated cone surface 23. When in use, the respiratory exhaust gas first enters the front exhaust section 41 through the gas chamber, then enters the rear exhaust section 42, and is discharged from the rear exhaust section 42. With the structural features of the second wall surface 12 and the truncated cone surface 23, the rear exhaust section 42 is formed into a horn shape surrounding the elbow 3, so that the respiratory exhaust gas is diverged and discharged all around the elbow 3.

Figure 14:
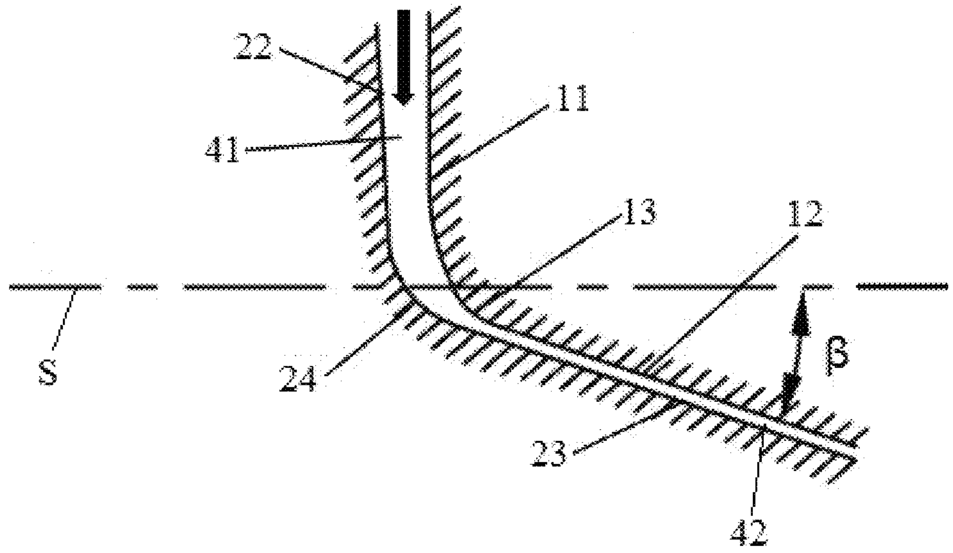
FIG. 14 is a schematic view of a first embodiment of an exhaust passage of the present disclosure.
Figure 15:
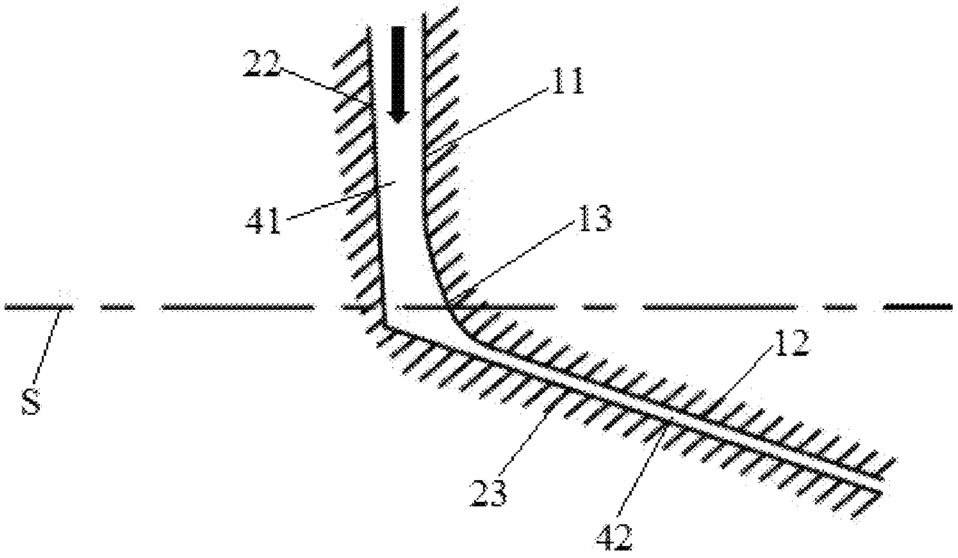
FIG. 15 is a schematic view of a second embodiment of the exhaust passage of the present disclosure.
Figure 16:
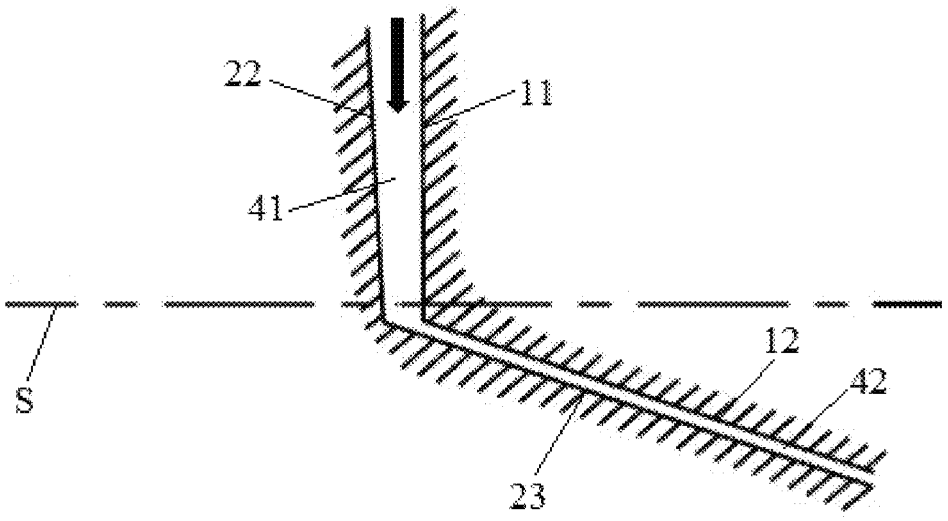
FIG. 16 is a schematic view of a third embodiment of the exhaust passage of the present disclosure.
Figure 17:
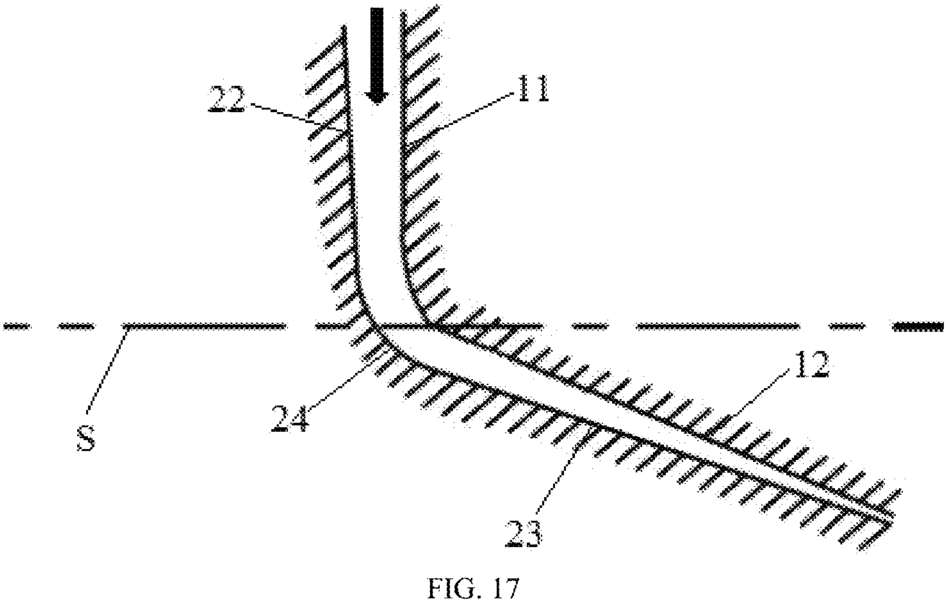
FIG. 17 is a schematic view of a fourth embodiment of the exhaust passage of the present disclosure.
Figure 18:
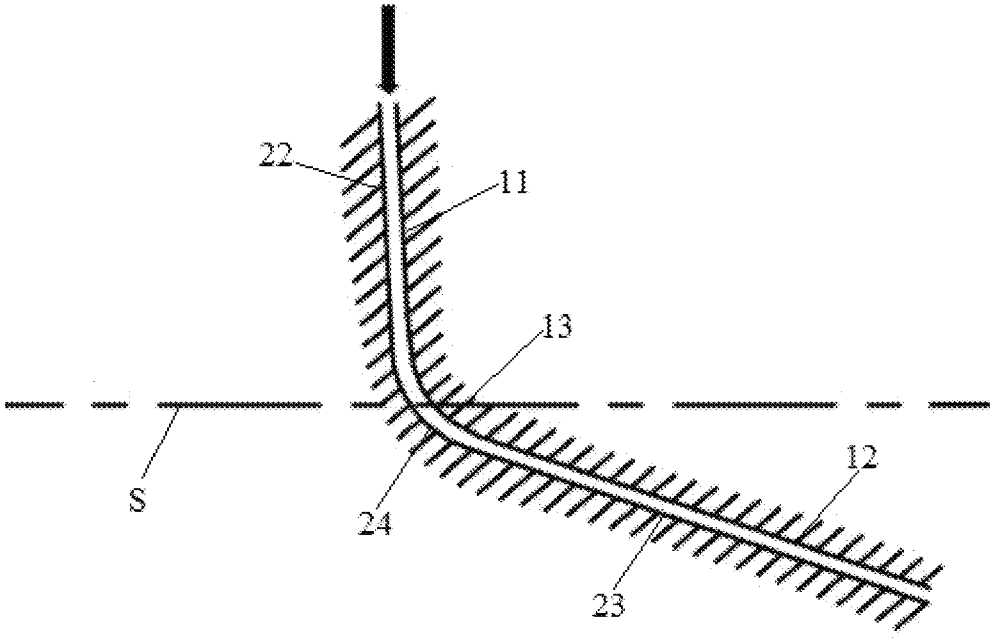
FIG. 18 is a schematic view of a fifth embodiment of the exhaust passage of the present disclosure.

It should be noted that regarding the aforementioned, the exhaust passage 4 may have various cross-sectional shapes, such as those shown in FIGS. 14-18, according to the difference in the transition modes between the first wall surface 11 and the second wall surface 12 as well as between the cylindrical surface 22 and the truncated cone surface 23, and the difference in an extending direction of a generatrix of the truncated cone surface 23 and that of the second wall surface 12. In order to ensure flowing continuity and smoothness of the respiratory exhaust gas, reduce flow resistance and reduce noise, it may be preferable that the first wall surface 11 and the second wall surface 12 are transitionally connected by a first arc 13 so that the cylindrical surface 22 is transitionally connected to the truncated cone surface 23 by a second arc 24 (see FIGS. 14 and 18). In order to facilitate control of the volume of exhaust gas, it may be preferable to make a width of the front exhaust section 41 larger than a width of the rear exhaust section 42, for example, as shown in FIG. 14. When the respiratory mask is worn, a plane approximately parallel to the patient's face may be denoted as a plane S. The front exhaust section 41 is connected with the nose of the patient. The front exhaust section 41 with a larger width facilitates discharge of the respiratory exhaust gas, and the rear exhaust section 42 with a smaller width facilitates controlling the volume of exhaust gas and reducing the exhaust noise. The generatrix of the truncated cone cavity forms an angle β with a bottom surface of the truncated cone cavity (which is parallel to the plane S). In order to prevent the discharged airflow from disturbing the bed partner, β may be 0-75°, preferably 10-30°. It can be understood that by adjusting the width of the rear exhaust section 42, the volume of exhaust gas can be adjusted and the exhaust noise can be reduced, and by adjusting the angle between the rear exhaust section 42 and the plane S, an adjustment of the exhaust direction can be achieved.

In the present disclosure, in order to improve the reliability of assembling the connector 2 with the frame 1 and reduce the degree of freedom of an axial movement of the connector 2 after assembly, a second protrusion 231 may be protrudingly formed on the truncated cone surface 23, and a second surface of the second protrusion 231 facing away from the truncated cone surface 23 is arranged to abut against the second wall surface 12; or a second protrusion 231 is protrudingly formed on the second wall surface 12, and a second surface of the second protrusion 231 facing away from the second wall surface 12 is arranged to abut against the truncated cone surface 23. In other words, the second protrusion 231 is provided in the rear exhaust section 42 and supported between the truncated cone surface 23 and the second wall surface 12. A protruding height of the second protrusion 231 determines the width of the rear exhaust section 42.

Figure 12:
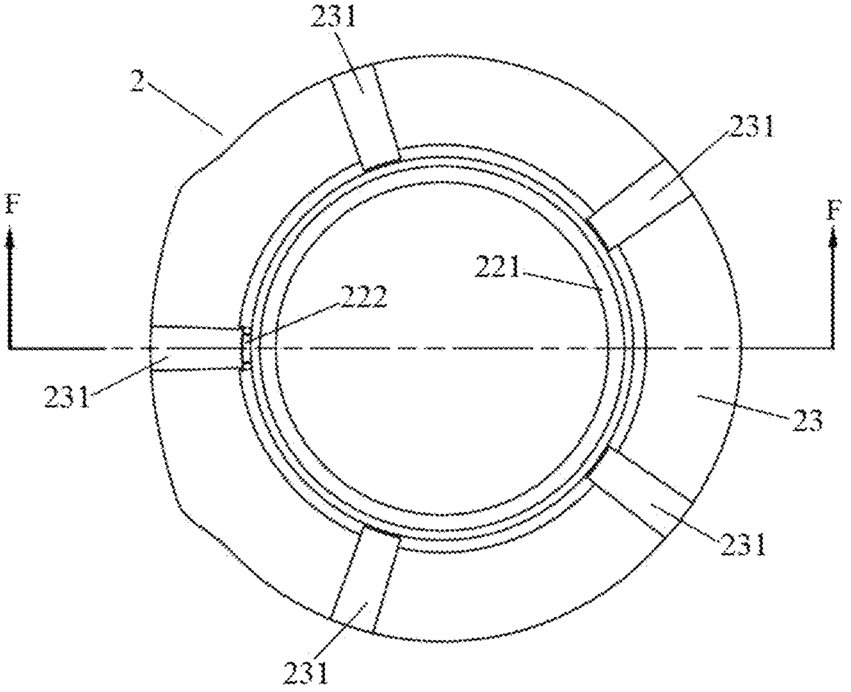
FIG. 12 is a top view of the connector in FIG. 11.

In order to further ensure the volume of exhaust gas and reduce the exhaust noise, preferably, the generatrix of the truncated cone surface 23 may be set parallel to the generatrix of the truncated cone cavity. The protruding height of the second protrusion 231 (that is, the width of the rear exhaust section 42) may be 0.05 mm-0.6 mm, preferably 0.05 mm-0.2 mm. In addition, in order to further enhance the effect, a plurality of the second protrusions 231 may be provided on the truncated cone surface 23 or the second wall surface 12, which are spaced apart in a circumferential direction of the truncated cone surface 23 or the second wall surface 12 (see FIG. 12). In this case, the plurality of second protrusions 231 may divide the rear exhaust section 42 into a plurality of fan-shaped passages.

In the present disclosure, the connector 2 may be connected to the frame 1 through a snap-fit structure, and the snap-fit structure may include a first buckle provided on the outer wall surface and a second buckle provided on the frame 1 and fitting the first buckle.

Figure 7:
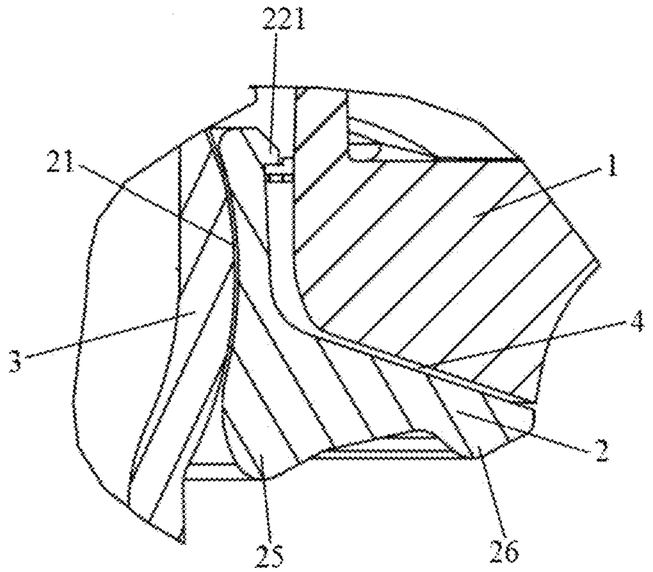
FIG. 7 is an enlarged view of part C in FIG. 6.

Specifically, according to an embodiment of the present disclosure, as shown in FIGS. 6 and 7, the first buckle is an annular boss 221 protrudingly formed on the cylindrical surface 22 and extending in a circumferential direction of the cylindrical surface 22. The second buckle is a first protrusion 111 protrudingly formed on the first wall surface 11. The connector 2 bears against the first protrusion 111 through the annular boss 221.

When assembling, referring to FIG. 6, an upper end of the connector 2 may be inserted into the installation cavity of the frame 1 from bottom to top, so that the annular boss 221 is clamped above the first protrusion 111 (for bearing an axial pull-off force). In order to facilitate installation of the annular boss 221 and ensure that the annular boss 221 is not easily loosened, a width of the annular boss 221 may be set to 0.1 mm-1 mm, preferably 0.2 mm-0.6 mm.

For the first protrusion 111, a first surface 112 of the first protrusion 111 facing away from the first wall surface 11 may be arranged to abut against the cylindrical surface 22, so that the first protrusion 111 can be supported between the first wall surface 11 and the cylindrical surface 22, thereby ensuring the reliability of assembling the connector 2 and the frame 1 and reducing the degree of freedom of the movement of the connector 2 after assembly. A protruding height of the first protrusion 111 may determine the width of the front exhaust section 41. In addition, in order to achieve a firm snap-fit with the annular boss 221, increase the ability of bearing pressure of the first protrusion 111 and facilitate discharge of the respiratory exhaust gas, as shown in FIG. 9, a width of the first protrusion 111 may be set to gradually increase in a direction toward the annular boss 221 (that is, the direction from bottom to top) in an axial direction of the cylindrical cavity. That is, the first protrusion 111 is structured with a wide upper part and a narrow lower part, and an included angle between a side surface 114 of the first protrusion 111 and a vertical direction may be 2°-6°. In addition, in order to achieve a smooth transition of the airflow between the front exhaust section 41 and the rear exhaust section 42, as shown in FIG. 9, an end of the first surface 112 of the first protrusion 111 facing away from the first wall surface 11, which is close to the second wall surface 12 (i.e., a lower end of the first surface 112), may extend to the second wall surface 12 and may be coplanar with the second wall surface 12.

Figure 8:
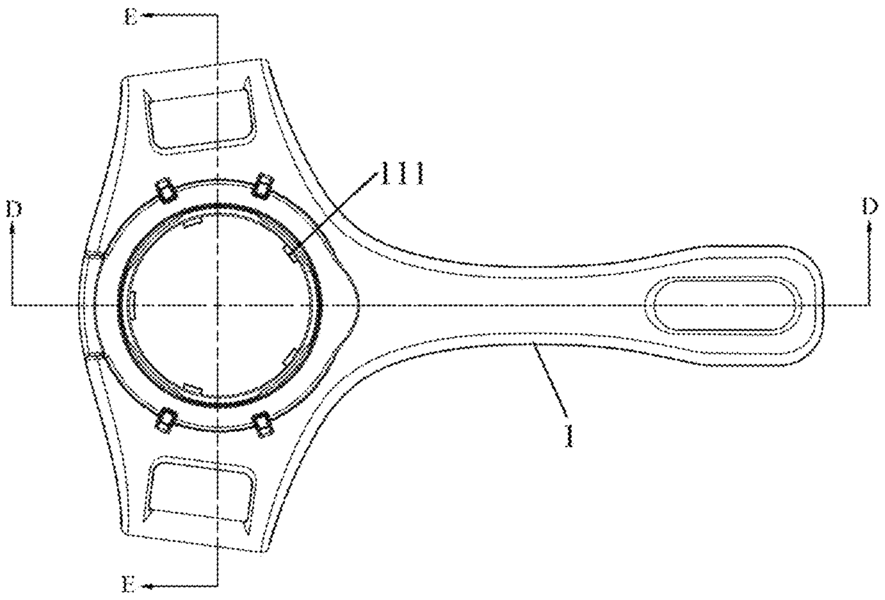
FIG. 8 is a top view of an embodiment of a frame of the present disclosure.

In the present disclosure, preferably, a plurality of the first protrusions 111 may be provided on the first wall surface 11, and the plurality of the first protrusions 111 may be spaced apart in the circumferential direction of the first wall surface 11 (see FIG. 8). It should be noted that the number of the first protrusions 111 may be equal to or different from the number of the second protrusions 231. Preferably, the number of the first protrusions 111 is equal to the number of the second protrusions 231, and the plurality of the second protrusions 231 correspond to the plurality of the first protrusions 111 in a one-to-one correspondence in the axial direction of the installation cavity, which can improve the reliability of assembling the connector 2 and the frame 1, guarantee a balanced force and meanwhile divide the entire exhaust passage 4 into a plurality of spaced-out flow passages.

In the present disclosure, in order to prevent the connector 2 from rotating relative to the frame 1, the respiratory mask may further include an anti-rotation structure for preventing the connector 2 from rotating relative to the frame 1. The anti-rotation structure may be implemented in any way, to which the present disclosure does not impose any limitation.

Figure 10:
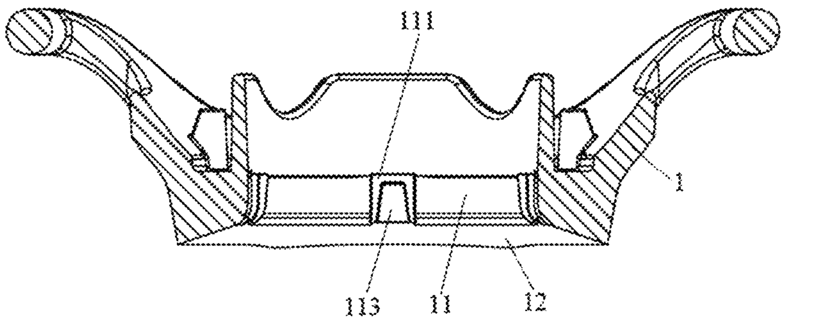
FIG. 10 is a cross-sectional view taken along line E-E in FIG. 8.

According to an embodiment of the present disclosure, as shown in FIGS. 10 and 11, the anti-rotation structure may include a flange 222 protrudingly formed on the cylindrical surface 22 and a groove 113 formed on the first protrusion 111 for embedding by the flange 222. It should be noted that if the frame 1 includes a plurality of first protrusions 111, the groove 113 is provided on one of the first protrusions 111. In addition, in order to facilitate the fitting between the flange 222 and the groove 113 during the assembling, a mark portion 27 (see FIG. 13) may be provided on the connector 2, with a position of the mark portion 27 corresponding to the flange 222 in a vertical direction. In this way, the assembling speed of the connector 2 and the frame 1 can be accelerated.

In the present disclosure, as to the connection between the elbow 3 and the connector 2, as shown in FIG. 6, the elbow 3 may be ball-socket connected to the inner wall surface 21 of the connector 2. In order to prevent the elbow 3 from being disengaged from the connector 2, a first convex portion 25 may be provided on a bottom surface of the connector 2; in order to improve the strength of the connector 2, a second convex portion 26 may be provided on the bottom surface of the connector 2. As shown in FIG. 6, the first convex portion 25 and the second convex portion 26 may be arranged to extend in the circumferential direction of the connector 2, and the first convex portion 25 and the second convex portion 26 may be respectively located at an inner rim and an outer rim of the bottom surface of the connector 2.

Another aspect of the present disclosure provides a ventilation therapy apparatus, which includes a host for generating a therapeutic gas and a respiratory mask in communication with a gas outlet of the host, and the respiratory mask is the above-mentioned respiratory mask.

The ventilation therapy apparatus may be a respirator.

The preferred embodiments of the present invention are described in detail above with reference to the accompanying drawings. However, the present invention is not limited to the specific details in the above-mentioned embodiments. Within the scope of the technical concept of the present invention, many simple modifications can be made to the technical solutions of the present invention. These simple modifications all belong to the protection scope of the present invention.

In addition, it should be noted that the various specific technical features described in the foregoing specific embodiments can be combined in any suitable manner, provided that there is no contradiction. In order to avoid unnecessary repetition, various possible combinations are not described separately in the present invention.

In addition, various different embodiments of the present invention can also be combined arbitrarily, as long as they do not violate the idea of the present invention, they should also be regarded as the disclosed content of the present invention.

The invention claimed is:

1. A respiratory mask, comprising a cushion assembly, an elbow assembly, and a connecting assembly arranged between the cushion assembly and the elbow assembly, wherein the cushion assembly comprises a cup, the connecting assembly comprises a frame and a connector, and the elbow assembly comprises an elbow, and wherein an exhaust passage is formed between the connector and the frame and/or between the cup and the frame, and the exhaust passage is arranged to be able to guide a respiratory exhaust gas to be diverged and discharged all around the elbow;

the connector has an outer wall surface for connecting with the frame, and the exhaust passage is formed between the outer wall surface and the frame;

the frame comprises an installation cavity for installing the connector, the installation cavity comprises a cylindrical cavity and a truncated cone cavity that are coaxial and in communication with each other, the truncated cone cavity is arranged close to the elbow, and the frame further comprises a first wall surface for defining the cylindrical cavity and a second wall surface for defining the truncated cone cavity;

the outer wall surface of the connector comprises a cylindrical surface corresponding to the first wall surface and a truncated cone surface corresponding to the second wall surface, gaps are provided in a radial direction of the installation cavity between the first wall surface and the cylindrical surface as well as between the second wall surface and the truncated cone surface, and the gaps form the exhaust passage;

a second protrusion is protrudingly formed on the truncated cone surface, and a second surface of the second protrusion facing away from the truncated cone surface is arranged to abut against the second wall surface; and a width of a rear exhaust section formed by the gap between the second wall surface and the truncated cone surface gradually narrows;

wherein the connector is connected to the frame through a snap-fit structure, and the snap-fit structure comprises a first buckle provided on the outer wall surface and a second buckle provided on the frame and fitting with the first buckle;

the first buckle is an annular boss protrudingly formed on the cylindrical surface and extending in a circumferential direction of the cylindrical surface, the second buckle is a first protrusion protrudingly formed on the first wall surface, and the connector bears against the first protrusion through the annular boss;

the respiratory mask further comprises an anti-rotation structure for preventing the connector from rotating relative to the frame;

the anti-rotation structure comprises a flange protrudingly formed on the cylindrical surface and a groove formed on the first protrusion for embedding by the flange; and a mark portion is provided on a bottom surface of the connector, with a position of the mark portion corresponding to the flange in a vertical direction.

2. The respiratory mask according to claim 1, wherein a diameter of the truncated cone cavity increases gradually in a direction away from the cylindrical cavity, and the first wall surface and the second wall surface are transitionally connected by a first arc; and/or the cylindrical surface and the truncated cone surface are transitionally connected by a second arc.

3. The respiratory mask according to claim 1, wherein an included angle β between a generatrix of the truncated cone cavity and a bottom surface of the truncated cone cavity is 0°-75°.

4. The respiratory mask according to claim 1, wherein a generatrix of the truncated cone surface is parallel to a generatrix of the truncated cone cavity, and a protruding height of the second protrusion is 0.05 mm-0.6 mm; and/or the truncated cone surface or the second wall surface is provided with a plurality of the second protrusions spaced apart in a circumferential direction of the truncated cone surface or the second wall surface.

5. The respiratory mask according to claim 1, wherein:

a width of the first protrusion gradually increases in a direction toward the annular boss in an axial direction of the cylindrical cavity; and/or an end of a first surface of the first protrusion facing away from the first wall surface, which is close to the second wall surface, extends to the second wall surface and the end is coplanar with the second wall surface.

6. The respiratory mask according to claim 1, wherein a plurality of first protrusions are provided on the first wall surface, the plurality of first protrusions are spaced apart in a circumferential direction of the first wall surface, and the groove is provided on one of the plurality of first protrusions.

7. A ventilation therapy apparatus, comprising a host for generating a therapeutic gas, and a respiratory mask in communication with a gas outlet of the host, wherein the respiratory mask is the respiratory mask according to claim 1.

8. A respiratory mask, comprising a cushion assembly, an elbow assembly, and a connecting assembly arranged between the cushion assembly and the elbow assembly, wherein the connecting assembly comprises a frame and a connector, the elbow assembly comprises an elbow, an exhaust passage is formed between the connector and the frame and/or between the cushion assembly and the frame, and the exhaust passage is arranged to be able to guide a respiratory exhaust gas to be diverged and discharged all around the elbow;

the connector has an outer wall surface for connecting with the frame, and the exhaust passage is formed between the outer wall surface and the frame;

the frame comprises an installation cavity for installing the connector, the installation cavity comprises a cylindrical cavity and a truncated cone cavity that are coaxial and in communication with each other, the truncated cone cavity is arranged close to the elbow, and the frame further comprises a first wall surface for defining the cylindrical cavity and a second wall surface for defining the truncated cone cavity;

the outer wall surface of the connector comprises a cylindrical surface corresponding to the first wall surface and a truncated cone surface corresponding to the second wall surface, gaps are provided in a radial direction of the installation cavity between the first wall surface and the cylindrical surface as well as between the second wall surface and the truncated cone surface, and the gaps form the exhaust passage;

a second protrusion is protrudingly formed on the truncated cone surface, and a second surface of the second protrusion facing away from the truncated cone surface is arranged to abut against the second wall surface; and a width of a rear exhaust section formed by the gap between the second wall surface and the truncated cone surface gradually narrows;

wherein the connector is connected to the frame through a snap-fit structure, and the snap-fit structure comprises a first buckle provided on the outer wall surface and a second buckle provided on the frame and fitting with the first buckle;

the first buckle is an annular boss protrudingly formed on the cylindrical surface and extending in a circumferential direction of the cylindrical surface, the second buckle is a first protrusion protrudingly formed on the first wall surface, and the connector bears against the first protrusion through the annular boss;

the respiratory mask further comprises an anti-rotation structure for preventing the connector from rotating relative to the frame;

the anti-rotation structure comprises a flange protrudingly formed on the cylindrical surface and a groove formed on the first protrusion for embedding by the flange; and a mark portion is provided on a bottom surface of the connector, with a position of the mark portion corresponding to the flange in a vertical direction.

9. The respiratory mask according to claim 8, wherein a diameter of the truncated cone cavity increases gradually in a direction away from the cylindrical cavity, and the first wall surface and the second wall surface are transitionally connected by a first arc, and/or the cylindrical surface and the truncated cone surface are transitionally connected by a second arc.

10. The respiratory mask according to claim 8, wherein an included angle β between a generatrix of the truncated cone cavity and a bottom surface of the truncated cone cavity is 0°-75°.

11. A ventilation therapy apparatus, comprising a host for generating a therapeutic gas, and a respiratory mask in communication with a gas outlet of the host, wherein the respiratory mask is the respiratory mask according to claim 8.

* * * * *